United States Patent [19]

Patel

[11] Patent Number: 4,769,029
[45] Date of Patent: Sep. 6, 1988

[54] PROSTHETIC GRAFT FOR ARTERIAL SYSTEM REPAIR

[76] Inventor: Jayendrakumar I. Patel, 502 Rector St., Valdese, N.C. 28690

[21] Appl. No.: 64,005

[22] Filed: Jun. 19, 1987

[51] Int. Cl.⁴ ............................ A61F 2/06; A61F 2/04
[52] U.S. Cl. .................................. 623/1; 128/334 R; 623/12
[58] Field of Search ............... 128/334 R, 334 C, 335, 128/325; 623/1, 12, 66

[56] References Cited

U.S. PATENT DOCUMENTS

| | | | |
|---|---|---|---|
| 3,435,824 | 4/1969 | Gamponia | 128/334 R |
| 3,853,126 | 12/1974 | Schulte | 623/66 X |
| 4,190,909 | 3/1980 | Ablaza | 128/334 R X |
| 4,441,215 | 4/1984 | Kastee | 128/334 R X |
| 4,705,517 | 11/1987 | DiPisa, Jr. | 623/1 X |

Primary Examiner—Richard J. Apley
Assistant Examiner—Alan W. Cannon
Attorney, Agent, or Firm—Roy B. Moffitt

[57] ABSTRACT

A prosthetic graft for arterial system repair comprising a flexible tube, an anchoring device attached at each of the two opposite ends of the flexible tube member, each anchoring device containing a ring, a circular member and a connecting member, in each anchoring device, the ring is connected to and defines an opening into one of the opposite ends of the flexible tube member, the circular member is spaced apart from the ring delimiting a space therebetween and the connecting member is affixed to the ring and the circular member spacing apart these two members.

12 Claims, 2 Drawing Sheets

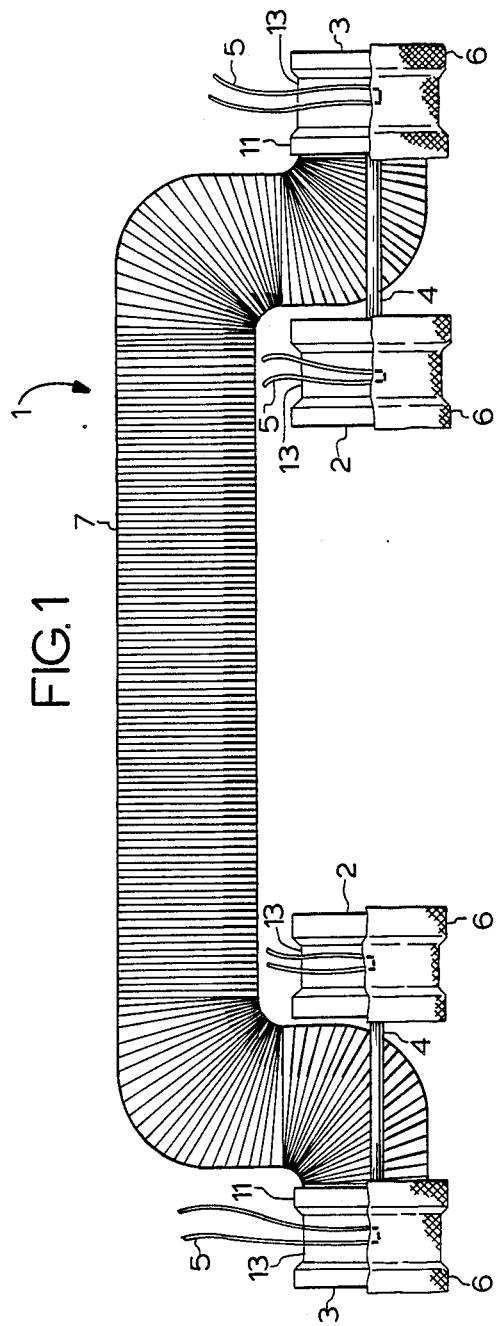
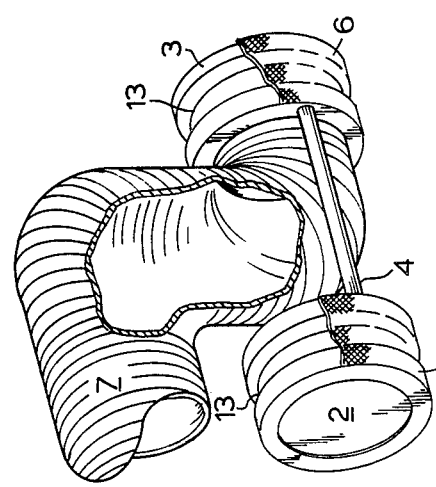

PROSTHETIC GRAFT FOR ARTERIAL SYSTEM REPAIR

BACKGROUND OF THE INVENTION

This invention relates to a device and method for the repair of ducts in a living body, for example the arterial system. It has been long recognized both in the medical profession and others that damage to a portion of the arterial system which carries blood from the heart to the various parts of the body is a significant cause of disability and death. Of particular concern are aneurysms and blockages in the aorta, the main trunk of the arterial system, the trunk that conveys blood from the left ventrical of the heart to all of the body except the lungs.

Significant advances have been made in recent years in medical and surgical arts towards the solution of this problem. One such solution is directed towards a procedure where a portion of the artery or aorta, in which the aneurysm occurs, is cut away or "resected" and a tubular "graft" is substituted for the resected segment. Generally this graft is a fabric tube, corresponding in diameter to the resected artery segment. After the tube or graft is set in place, it is then sutured at its opposite ends to the adjacent edges of the artery. More recent advances in the medical and surgical art in this area have employed a graft and a method of using it which obviates the necessity of resection and which utilizes the arterial walls of the segment containing the aneurysms or other defects to reenforce and strengthen the graft. Such a solution is shown in U.S. Pat. No. 4,190,909, which discloses a prosthetic graft in the form of a flexible tube with a rigid end portion, each of the rigid end portions having an annular groove therein. The graft is used by slitting a portion of an artery containing an aneurysm or other damage to form an opening, inserting the graft through the opening into the artery, positioning the graft longitudinally within the artery, and circumferentially ligating the artery against the grooves in the rigid end portion of the graft. This procedure requires that the graft be inserted inside of the artery and the artery sutured around the graft. When the known prior art method and apparatus is used, it can only be employed when the artery is dilated, as in the case of an aneurysm of an artery. It cannot be employed when the artery is partially or completely blocked due to narrowing of its lumen from clots or arteriosclerosis.

When narrowing or blockage occurs in a duct such as an artery or vein, prior art prosthetic grafts are placed outside the artery and connected to the artery at both ends with manually applied sutures. In dealing with very narrow or small sized arteries (one millimeter in diameter or less) this suturing sometimes is accomplished by means of a glue. In larger arteries like the aorta, manual suturing has to be done to make the connections between the ends of a prosthetic graft and the artery. This suturing is sometimes technically difficult and time consuming and requires prolonged clamping of the artery during suturing to prevent blood loss, with obvious resulting adverse effects.

Contrary to the known prior art, the present invention is one that provides a multi-anchored connection between the artery and the prosthetic graft. It is particularly useful where the prosthetic graft, shown in U.S. Pat. No. 4,190,909, cannot be used because the graft must be placed outside an artery which is substantially blocked. The present invention minimizes the time required in making a connection between a body tube (like an artery) and the prosthetic graft thereby minimizing the blood flow interruption to the body organs otherwise supplied by the artery. This greatly reduces the complications due to the lack of blood supply.

The present invention also makes it technically easier to make a connection between a body tube and the prosthetic graft, so that a less experienced surgeon may make a connection with skill and confidence.

The prior art disclosed prosthetic graft basically had two anchoring positions, one at one end of the graft and one at the other plus some anchoring that arose out of the suturing used to close the duct after the graft had been inserted. In the present invention, there are no less than six anchoring points to securely affix the grafts and reduce the risk of migration of the graft as a result of body movements and blood flow therethrough.

BRIEF DESCRIPTION OF THE INVENTION

The present invention is a prosthetic graft for arterial system repair comprising a flexible tube, an anchoring device attached at each of the two opposite ends of the flexible tube member, each anchoring device contains a ring, a circular member and a connecting member, in each anchoring device, the ring is connected to and defines an opening into one of the opposite ends of the flexible tube member, the circular member is spaced apart from the ring delimiting a space therebetween and the connecting member is affixed to the ring and the circular member spacing apart these two members.

BRIEF DESCRIPTION OF THE DRAWINGS

FIG. 1 is a side elevation of the invention disclosing a tubular flexible graft having an anchoring device on each end.

FIG. 2 is a prospective view of the elements of the anchoring devices of FIGS. 1 and 3.

DETAILED DESCRIPTION OF THE INVENTION

Figure 3:
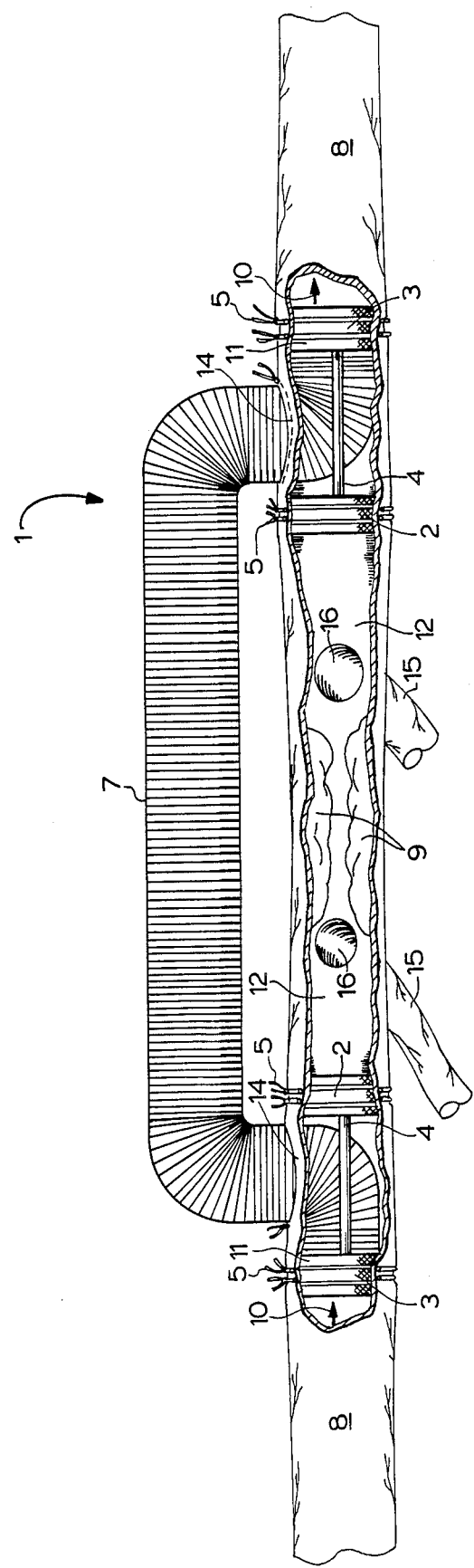
FIG. 3 is a side, partially cut-away, elevation of the graft of FIG. 1 secured in place in its intended environment, one anchoring device secured on one side of a vein or artery blockage and the other anchoring device secured at the other side.
Figure 4:
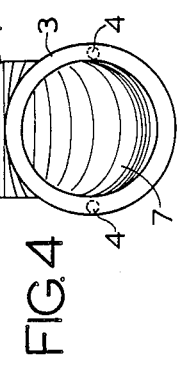
FIG. 4 is a side elevation of the view of FIG. 2.

Element 1 of FIG. 1 is a side elevation of the invention. It is composed of flexible tubular graft 7 having opposite ends, denoted by element 11. To each opposite end is affixed an anchoring device composed of circular or ring shaped device 3, circular or disc shaped device 2 and connecting member 4. Circular shaped members 2 and 3 can be made of metal or plastic (polymeric material) and are covered with a knitted velour, well known in the prior art. See U.S. Pat. No. 4,190,909. Circular member 3 is spaced apart from circular number 2, such elements being disposed opposite one another. Ring member 3 is connected to disc member 2 by connecting members 4, which also serve to space apart ring member 3 from disc member 2. Ligature 5 is passed through covering 6 on each ring 3 and disc member 2 by a needle (not shown) so that two legs of the ligature dangle free. By so doing, these two legs can be passed through vein or artery wall 8 so that they may be used to wrap around element 8 directly over annular groove 13 to secure the circular members in place. Alternatively, the ligature may circumferentially ligate the artery 8 against the annular groove 13 of the circular ring 3 and the disc 2. Ring member 3 is attached to graft 7 at junction 11 and is in communication with the interior of tubular graft member 7, which exits the artery through the space defined by the connector 4, ring 3 and disc 2. Thus, fluid flowing from the left to the right in FIG. 1 goes through ring member 3, through flexible tubular member 7 and thence out the right hand ring member 3. Circular member 2 is a disc and it serves as a blockage member. Any blood or fluid that may somehow find its way into the cavity identified by element 12, via intersecting veins through openings 16, would not be allowed to seep out into the body cavity because of the blockage nature of disc 2.

Graft 7 comprises a tube constructed of polymers such as "Dacron" type plastic. It is attached to ring 3 at juncture 11. Each circular member (elements 2 and 3) contains an annular groove in its exterior shown by element 13. As is known in the prior art, this groove creates a securing mechanism for the ligatures 5 to secure the anchoring devices to the duct sought to be repaired.

In FIG. 3, the invention is shown in its intended environment, i.e. a prosthetic graft to convey blood (see flow directional arrow 10) around artery blockage 9 and into an undamaged or healthy portion of artery 8 downstream from blockage 9. In FIG. 3, the prosthetic graft 1 of FIG. 1 is shown secured in place. In order to do this, artery 8 is first clamped (See U.S. Pat. No. 4,190,909) then two small openings are made in artery 8 on both sides of blockage 9. In one such opening there is inserted one anchoring device (elements 2 and 3 shown in the left-hand portions of FIG. 3) and a terminal portion of graft 7. In like manner, the right-hand anchoring device (elements 2, 3, and 4 shown in the right-hand portion of FIG. 3) is inserted in the other opening along with a terminal portion of the opposite end of flexible tubular graft 7. Once this is accomplished ligatures 5 are tied in place employing annular grooves 13 in the same manner as described in the prior art in the previously identified U.S. patent. Then suturing 14 may be performed if desired to affix artery 8 to flexible tubular member 7. Thus, at each terminal end of flexible tubular 7 there are three anchoring positions that anchor duct or artery 8 to the prosthetic 1, namely ligatures 5 of elements 2 and 3 and the suturing of suture 14 making a total of 6 anchoring positions. Prosthetic 1 may have a minimum of two terminal ends each containing an anchoring device (elements 2, 3 and 4) as shown in FIGS. 1 and 2 or it may have a multiplicity of branching terminal ends (not shown) each terminated by an anchoring device (elements 2, 3 and 4), all of which may but not necessarily converge into a single terminal portion having an anchoring device on it as shown. For each terminal end, there is an anchoring device and thus 3 anchoring sites. The procedure for use of such a multiterminal device is the same as shown in FIGS. 1, 2, 3, namely, an insertion of an anchoring device, tying off ligatures 5 and surturing artery wall 8 to the side wall of graft 7 forming 3 anchoring positions for each anchoring device. Obviously, artery or duct 8 must be first clamped (not shown) upstream and downstream from the area the anchoring devices are inserted into element 8. Such clamping is known and shown in the prior art by the previously identified U.S. patent.

By providing three anchoring positions for each anchoring device, a stable prosthetic is provided and the flow of blood through the prosthetic is less likely to disturb or move prosthetic 1 from its intended originally placed position when compared to known prior art devices. Although circular anchoring devices 2 and 3 may be constructed of stainless steel and although this may be preferred material because of the inherent characteristics of strength, noncorrosiveness, and the like, it is also possible to use other materials such as plastic (polymeric) or other metals, or other materials found to have the same or similar characteristics. The same is generally true of the materials used in construction of the flexible tubular body 7 and the coverings 6.

It is obvious and it is to be understood that although this invention has been described with reference to the repair of the arterial ducts having an aneurysm, the invention may be used for the repair of any ducts which may be otherwise damaged, or for ducts other than arterial ducts within the body. In addition, the invention is applicable to both human and other living bodies. It is also obvious that one can use separate ligatures rather than ligatures connected to the graft, although the connected ligatures are preferable because, after they are passed through the duct tissue, they can be used to align and retain the graft in position within the duct.

What is claimed is:

1. A prosthetic graft comprising:
   (a) first and second spaced apart circular shaped members disposed in face-to-face relationship to one another delimiting an open cylindrical-like space therebetween;
   (b) a connecting member affixed to a peripheral portion of the first and second circular shaped members and disposed therebetween, said connecting member being a means to space apart the first and second circular-shaped members; and,
   (c) a flexible tubular-shaped graft member having a body and first and second end portions, the first end portion affixed to the first circular shaped portion, a portion of the body of the graft member extending into said open cylindrical-like space between the first and second spaced-apart circular-shaped members.

2. The prosthetic graft of claim 1 wherein the second end portion of the tubular-shaped graft member lies outside of the cylindrical-like open space.

3. The prosthetic graft of claim 2 wherein the second circular-shaped member is disk shaped and the first circular member is ring shaped defining an opening in the first end portion of the flexible tubular-shaped graft member.

4. The prosthetic graft of claim 3 wherein the flexible tubular-shaped graft member is composed of polymeric material.

5. The prosthetic graft of claim 1 including third and fourth spaced apart circular-shaped members delimiting a cylindrical-like open space therebetween, each of said circular-shaped members has an outer most surface in which there is an angular grove, a second connecting member affixed to a peripheral portion of the third and fourth circular-shaped members and disposed therebetween, and the second end portion of the flexible tubular-shaped graft member is affixed to the third circular shaped member.

6. The prosthetic graft of claim 5 wherein the fourth circular-shaped member is disk shaped and the third circular-shaped member is ring shaped and defines an opening in the second end portion of the flexible tubular-shaped graft and there is communication between the first and third circular-shaped members.

7. The prosthetic graft of claim 6 wherein the tubular-shaped flexible graft member is composed of polymeric material.

8. A prosthetic graft comprising a flexible tube having opposite ends and an anchoring device attached at each of the opposite ends, each anchoring device contains a ring, a circular member and a connecting member, and in each anchoring device, the ring is connected to and defines an opening into one of the opposite ends of the flexible tube, the circular member is disposed in face-to-face relationship to the ring and is spaced apart from the ring delimiting a cylindrical-like open space therebetween, and the connecting member is disposed between and affixed to a peripheral portion of the ring and the circular member.

9. The prosthetic graft of claim 8 wherein a terminal portion of said flexible tubular member is disposed in the cylindrical-like open space.

10. The prosthetic graft of claim 8 wherein the flexible tube is composed of polymeric material.

11. The prosthetic graft of claim 8 wherein the circular-shaped member of each anchoring device is a disk.

12. The prosthetic graft of claim 8 wherein the rings of each anchoring device are composed of metal or plastic.

* * * * *